United States Patent
Westlund et al.

(10) Patent No.: US 8,337,792 B2
(45) Date of Patent: Dec. 25, 2012

(54) AROMATIC IMINE COMPOUNDS FOR USE AS SULFIDE SCAVENGERS

(75) Inventors: Gary Westlund, Pleasanton, CA (US); David Weller, Suisun City, CA (US)

(73) Assignee: Guard Products LLC, Oakland, CA (US)

( * ) Notice: Subject to any disclaimer, the term of this patent is extended or adjusted under 35 U.S.C. 154(b) by 0 days.

(21) Appl. No.: 13/186,132

(22) Filed: Jul. 19, 2011

(65) Prior Publication Data

US 2011/0271835 A1    Nov. 10, 2011

Related U.S. Application Data

(63) Continuation of application No. 11/854,069, filed on Sep. 12, 2007, now Pat. No. 7,985,881.

(51) Int. Cl.
*B01D 19/00* (2006.01)
*B01D 53/44* (2006.01)

(52) U.S. Cl. .................. 423/242.2; 423/242.1; 95/235; 95/237; 210/511

(58) Field of Classification Search .......... 423/220, 423/228, 242.1, 242.2; 564/446; 95/149, 95/230, 235, 237, 241; 210/511
See application file for complete search history.

(56) References Cited

U.S. PATENT DOCUMENTS

| 2,783,205 | A | | 2/1957 | Brooks et al. |
| 3,497,485 | A | * | 2/1970 | Emmons ................ 526/312 |
| 5,128,049 | A | | 7/1992 | Gatlin |
| 5,169,411 | A | * | 12/1992 | Weers ..................... 44/421 |
| 5,223,127 | A | | 6/1993 | Weers et al. |
| 5,266,185 | A | | 11/1993 | Weers et al. |
| 5,698,171 | A | * | 12/1997 | Trauffer et al. ............ 423/220 |
| 5,958,352 | A | | 9/1999 | Callaway et al. |
| 2002/0157989 | A1 | | 10/2002 | Gatlin et al. |
| 2008/0056974 | A1 | | 3/2008 | Salma et al. |

FOREIGN PATENT DOCUMENTS

| EP | 0475642 A | 3/1992 |
| EP | 0524723 A | 1/1993 |

* cited by examiner

*Primary Examiner* — Roy King
*Assistant Examiner* — Jared Wood
(74) *Attorney, Agent, or Firm* — King & Spalding LLP; Peter Dehlinger (57) ABSTRACT

Compositions and methods relating to aromatic imine compounds and methods of their use are described. The compounds are formed from aromatic aldehydes and amino or amino derivatives. The compounds and their derivatives are useful, for example, as hydrogen sulfide and mercaptan scavengers for use in both water and petroleum products.

5 Claims, 10 Drawing Sheets

IMINE AND ACETAL FORMATION

IMINE

HEMIACETAL

ACETAL

+

IMINE/ACETAL

ETHYLENE DIAMINE REACTIONS
WITH BENZALDEHYDE

+

→ SOLID POLYMER

+  +

→ STABILE EMULSION
CLEARS WITH ALCOHOL

+ 1/2  → RED DIMER LIKE PRODUCT

RED DIMER LIKE PRODUCT + 1/4  → BROWN LIQUID
88% SOLUBLE IN KEROSENE
FREEZES AT ROOM TEMP
INSOLUBLE IN WATER WITHOUT
SURFACTANTS AND SOLVENTS

Figure 6

REACTION OF CINNAMALDEHYDE AND ETHANOLAMINES

CINNAMALDEHYDE           ETHANOLAMINE

CINNAMALDEHYDE IMINE

+

CINNAMALDEHYDE ENAMINE
RING HAS 2 DOUBLE BONDS DISTRIBUTED
ACROSS 5 CARBONS AND IN RESONANCE
WITH THE CONJUGATED DOUBLE BONDS

BENZYL AMINE REACTION

BENZALDEHYDE                    BENZYL AMINE

TWO ALDEHYDE ADDITION
TRI AMINE COMPLEX ONE OF SEVERAL
DIFFERING RESONANCE STRUCTURES
AS MANY AS 36 RESONANCE STABILIZING
STRUCTURES

Figure 10

AROMATIC IMINE COMPOUNDS FOR USE AS SULFIDE SCAVENGERS

CROSS-REFERENCE TO RELATED APPLICATIONS

This application is a continuation of U.S. patent application Ser. No. 11/854,069, filed Sep. 12, 2007, to issue on Jul. 26, 2011 as U.S. Pat. No. 7,985,881, which is hereby incorporated by reference in its entirety.

TECHNICAL FIELD

The present compositions and methods relate to aromatic imine compounds and methods of use, thereof. The compounds and their derivatives are useful, for example, as hydrogen sulfide and mercaptan scavengers for use in both water and petroleum products.

BACKGROUND

Sulfides in the Environment

Petroleum and natural gas that occur naturally in the geologic formations beneath the earth's surface are often found to contain water, carbon dioxide, sulfur, hydrogen sulfide, and mercaptans. Hydrogen Sulfide and mercaptans (i.e., organic sulfides) have a strong, malodorous "rotten egg" smell, and are toxic. Products containing sulfides, including oil, natural gas, and water, are referred to as "sour." The levels of organic sulfides in natural gases depend on the source but range from about 0.1 part per million (ppm) to 150,000 ppm.

Both carbon dioxide and hydrogen sulfide are acid gases. They are corrosive in gaseous form and when dissolved in liquids. Transporting and containing acid gases posses a problem for steel piping and containers. Because of this corrosive hazard and the malodorous smell, producers of natural gas must remove sulfides before transport.

Typically, field processing plants are used to remove sulfides prior to transport. Processing plants used for natural gas may use bubble columns, packed columns, tray columns, and/or other methods to absorb the sulfides into a liquid product, by subjecting the gas to countercurrent flow in the presence of sulfide scavengers. Conventional sulfide scavengers are ethanolamines (used in a regenerating plant), triazines, formaldehyde, imines, glyoxal, and combinations, thereof.

Triazines are the most widely used scavengers in recent years, particularly those formed by the reaction of formaldehyde and monoethanolamine. Triazines are a complex chain of aldehyde-like molecules with a calculated molecular weight of about 219 g/mole (i.e., three aldehyde molecules). Triazines react with sulfides to form complex intermediates, and when used to the exhaustion of their reactive imino groups, they form solids. Triazines are popular because of their relative safety compared to formaldehyde, scavenging capacity, and low cost. However, triazines still contain free formaldehyde, which is a known carcinogen and health concern.

Sulfide contamination is endemic to the production of liquid oil and petroleum products. As sweet crude, which is relatively free of sulfur, becomes less available and more expensive, available oil supplies increasingly have some level of sulfur contamination, leading to the formation of hydrogen sulfide and mercaptans. Waste water (including sewage) can also be rich hydrogen sulfide and mercaptans. Heat and acids drive hydrogen sulfide into the air, creating a noxious and toxic environment, e.g., in oil refineries, sewage treatment plants, wastewater treatment facilities, etc.

Hydrogen sulfide and mercaptans are also produced in the putrefaction of organic matter, causing foul smells from brackish ponds, garbage storage areas, and trash collection facilities, and food establishments.

Sulfide Removal Methods

Because of the odor and health problems associated with sulfides, petroleum refiners, chemical cleaning contractors, garbage companies, food establishments, and other industries use methods to control or eliminate hydrogen sulfide and mercaptan emissions. For example, hydrogen sulfide may be scrubbed out of gas mixtures by contacting the gas with caustic alkaline compounds, which remove at least one of the hydrogen atoms, thereby reducing its volatility as a gas and producing a salt. Countercurrent gas flow against a liquid spray or stream through a tray column, packed column or tower is a particularly common method of sulfide removal. This process can also be used with ethanolamines in a recovery system.

Hydrogen sulfide present in gas or water may also be reacted with oxidizing agents such as potassium permanganate but such reactions encourage corrosion in systems and cannot be used with combustible fuels or their vapors.

Hydrogen Sulfide can be reacted with some aldehydes, triazines, imines, or imino compounds to create less odorous compounds. However, such compounds have low solubility in liquid petroleum products (crude oil, gasoline, kerosene, diesel, gear oil, hydraulic fluids, etc.).

The need exists for sulfide scavengers that are soluble in fuels and/or oils, that are efficient in removing hydrogen sulfide and mercaptans, and that are safe to transport and handle.

SUMMARY

The following aspects and embodiments thereof described and illustrated below are meant to be exemplary and illustrative, not limiting in scope.

In one aspect, a composition produced by reacting an aromatic aldehyde with an amine or amine derivative is provided, the composition characterized by having sulfide scavenger activity.

In some embodiments, the composition is soluble in water. In some embodiments, the composition is soluble in an organic solvent. In some embodiments, the composition is soluble in a petroleum product.

In some embodiments, the aromatic aldehyde is benzaldehyde, cinnamaldehyde, or a vanillin. In some embodiments, the amine or amine derivative is selected from monoethanolamine, ethylene diamine, benzylamine; glyoxal, and diglycol-amine.

In another aspect, a method for removing sulfide from a water is provided, comprising the step of contacting the gas with an amount of aromatic imine compound, thereby removing sulfide from the gas via reaction with the aromatic imine compound.

In some embodiments, the aromatic imine compound is produced by reacting an aromatic aldehyde with an amine or amine derivative.

In particular embodiments, the aromatic aldehyde is selected from benzaldehyde, cinnamaldehyde, and a vanillin. In particular embodiments, the amine or amine derivative is selected from monoethanolamine, ethylene diamine, benzylamine, glyoxal, and diglycol-amine.

In some embodiments, the aromatic aldehyde is benzaldehyde and the amine or amine derivative is monoethanolamine. In particular embodiments, the aromatic aldehyde is benzaldehyde and the amine or amine derivative is monoethanolamine, and the reacting is performed in the presence of water.

In some embodiments, the present composition and methods are used to treat water in a water treatment plant. In some embodiments, the present composition and methods are used to treat water in a sewage treatment plant.

In a related aspect, a method for removing sulfide from a gas is provided, comprising the step of contacting the gas with an amount of aromatic imine compound, thereby removing sulfide from the gas via reaction with the aromatic imine compound.

In some embodiments, the aromatic imine compound is produced by reacting an aromatic aldehyde with an amine or amine derivative. In some embodiments, the aromatic aldehyde is selected from benzaldehyde, cinnamaldehyde, and a vanillin. In some embodiments, the amine or amine derivative is selected from monoethanolamine, ethylene diamine, benzylamine, glyoxal, and diglycol-amine.

In some embodiments, the contacting is performed is using the aromatic imine compound immobilized to a solid support. In some embodiments, the contacting is performed is using solid or semi-solid aromatic imine compound.

In another aspect, a method of producing a triazine compound is provided, comprising reacting an aromatic aldehyde with an amine or amine derivative to produce an aromatic imine compound, and then reacting the aromatic imine compound with glyoxal and an amine.

In some embodiments, the aromatic aldehyde is benzaldehyde and the amine or amine derivative is monoethanolamine.

In another aspect, a triazine compound produced by the present method is provided.

These and other objects and features of the invention are made more fully apparent in the following detailed description of the invention.

DETAILED DESCRIPTION

I. Definitions

As used herein, the term "aromatic imine compound" refers to a compound (or plurality of compounds) formed in a reaction between an aromatic aldehyde and a primary or secondary amine or amine derivative. The compounds may morph between a plurality of meta-stable forms, including imines, enamines, hemi-acetals, acetal, and amine/acetal. Aromatic imine compounds may also form multimers.

As used herein, an "aromatic aldehyde" is an aldehyde with an aromatic ring group attached and lacking a reactive aliphatic alpha hydrogen (i.e., a hydrogen on the alpha carbon). Preferred aromatic aldehydes have the aldehyde group attached directly to the aromatic ring (e.g., in the case of benzaldehyde), or attached to an allylic carbon (i.e., C=C) that is attached to the aromatic ring (e.g., in the case of cinimaldehyde).

As used herein, an "aromatic acetal" is an aromatic compounds with an ether or di-ether linkage between the carbonyl carbon and another functional group of the molecule.

As used herein, "mercaptans" or "thiols" are organic compounds resembling alcohols but having the hydroxyl group replaced by a sulfhydryl group (i.e., —SH rather than —OH).

As used herein, "a multimer" is a dimer or a polymer.

With reference to molecules having several resonance structures, such molecule are said to "exist" in each and all of their resonance structure (i.e., tautomers). It is understood that a molecule may morph into other tautomers.

The use of the singular article forms "a" and "an" and the single forms of other nouns includes the plural unless otherwise specified or apparent.

Terms not defined should be given their ordinary meaning.

II. Aromatic Aldehydes

Aromatic aldehydes are characterized by having the structure where Ph is an aromatic substituent, including but not limited to any of the following:

The aromatic aldehyde may be substituted such that each R group (e.g., $R^1$-$R^5$ of the phenyl substituent shown below) is independently selected from, hydrogen, alkyl, alkyloxy, ester, amino, hydroxyl, aldehyde, carboxylic acid, sulfonic acid, phosphoric acid, and halide. Exemplary R groups are —H, —$CH_3$, —$OCH_3$, —$OCH_2CH_3$, —$NH_2$, —OH, —$NHR^6$, —CHO, —COOH, —$COOR^7$, —$(CH_2)_nCH_3$, —Cl, —Br, —I, —$SO_3H$, —$SO_3R^8$, and combinations thereof. $R^6$-$R^8$ independently selected and similar substituents, and n is an integer.

In alcoholic solutions, aldehydes generally exist in equilibrium with hemiacetals and acetals. High alcohol/low water concentrations shift the equilibrium in the direction of the acetal. Low alcohol/high water concentrations shift the equilibrium in the direction of the aldehyde. Acid and water hydrolyze the acetal and return the compound to the aromatic aldehyde and alcohol starting materials. These reactions are illustrated below (note that all reactions are reversible, although the arrows indicate a single direction).

Aromatic aldehydes are suited for the production of the present aromatic imine compounds because, when the aldehyde group is attached directly to the aromatic group, they do not have an alpha hydrogen available to allow the aromatic aldehyde to react with itself. Other aromatic aldehydes in which the aldehyde group is not attached directly to the aromatic group but, rather, attached via an allylic carbon, behave in a similar manner, and are also suitable for use as described. The absence of a reactive alpha hydrogen avoids acid or base-catalyzed aldol condensation and Claisen condensation, which occurs with aldehydes and ketones that contain alpha hydrogens, and produces longer chain compounds. Aromatic imine compounds are stable in basic solutions and in some acid solutions.

II. Aromatic Imine Compounds

The present compositions and methods relate to a class of aromatic imine compounds, methods for their synthesis, and methods for their use. The compounds are formed by reacting an aromatic aldehyde with a primary or secondary amine or amine derivative, thereby producing a meta-stable, aromatic imine compound. Where tested, it was found that the reaction product had a lower flash point than either starting material, which is unexpected from a product of an exothermic reaction.

Figure 1:
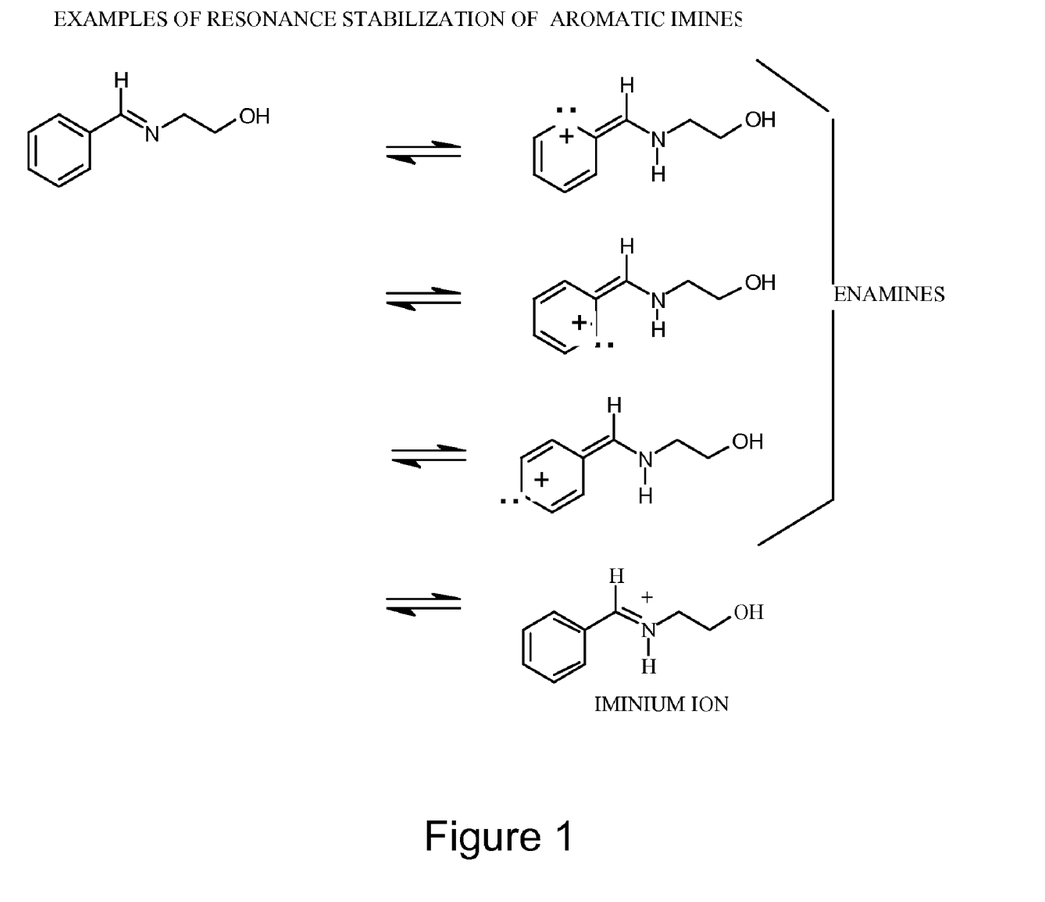
FIG. 1 shows examples of resonance structures formed by aromatic imines.

Without being limited to a theory, it is suggested that the aromatic imine compounds morph between different resonance structures, forming an equilibrium of imines, enamines, acetals, hemi-acetals, and amine/acetals, or dimers or polymers (i.e., multimers) thereof. Imines and enamines are tautomers having the structures shown in FIG. 1. Imines have a carbon-nitrogen double-bond, while enamines have a carbon-carbon double-bond at the alpha carbon and a single carbon-nitrogen bond. In aryl enamines, the benzene ring has a double-bond to the carbonyl carbon and is stabilized by multiple resonance structures.

Figure 2:
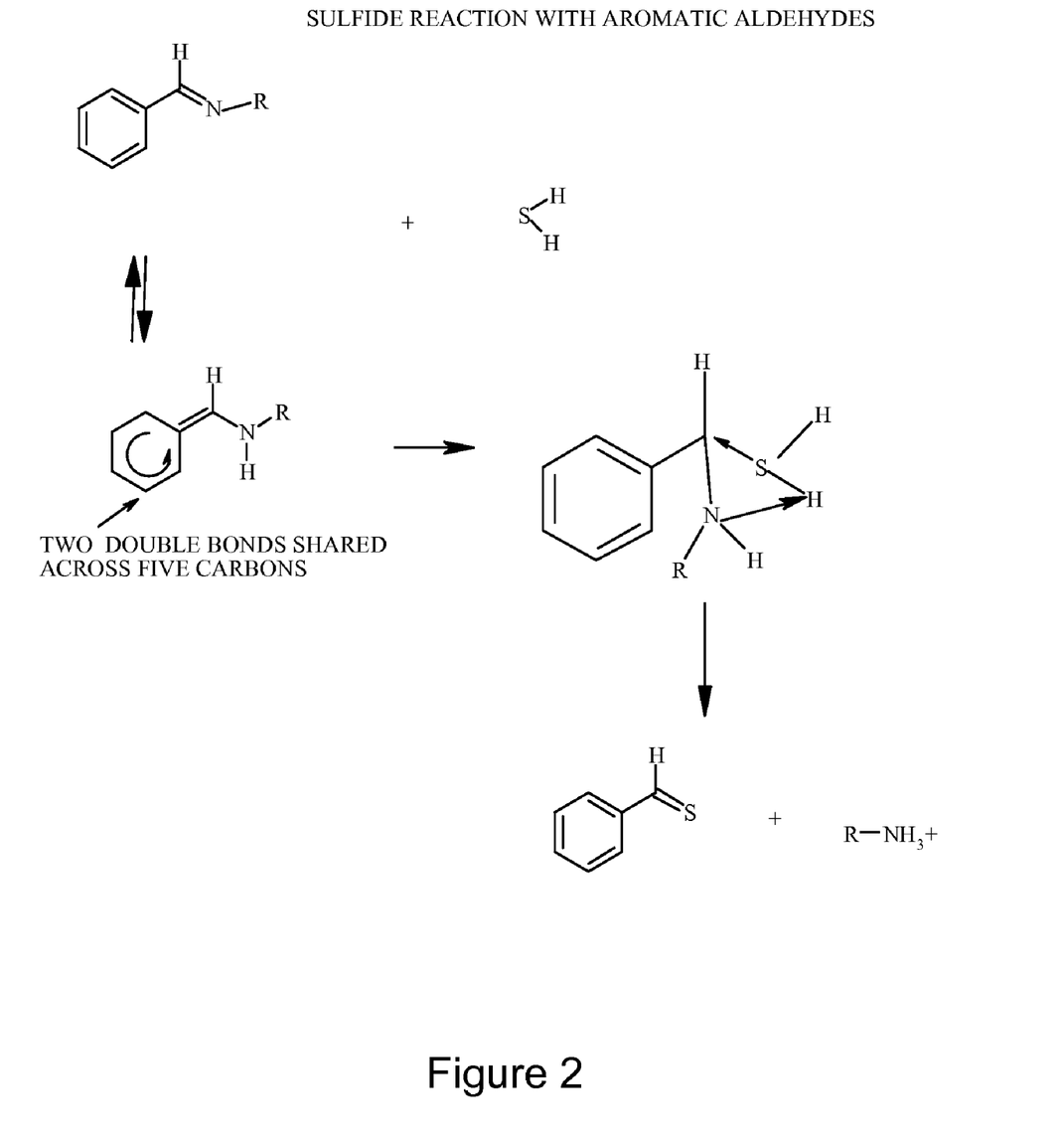
FIG. 2 shows a reaction between an aromatic aldehyde and hydrogen sulfide.

Aryl enamines are more reactive than the corresponding imine structures because reactive groups are drawn to the carbon atom with reduced electron density as a result of a proximal electron withdrawing group (such as a protonated amine). A proposed reaction between an aromatic imine compound and a sulfide is shown in FIG. 2. According to the diagram, the enamine is the most reactive tautomer. The reaction produces an odorless aromatic sulfide and regenerates the amine or amine derivative. Such tautomeric rearrangements, and their effect on reactivity and solubility, are believed to be a feature of the present compounds.

Figure 3:
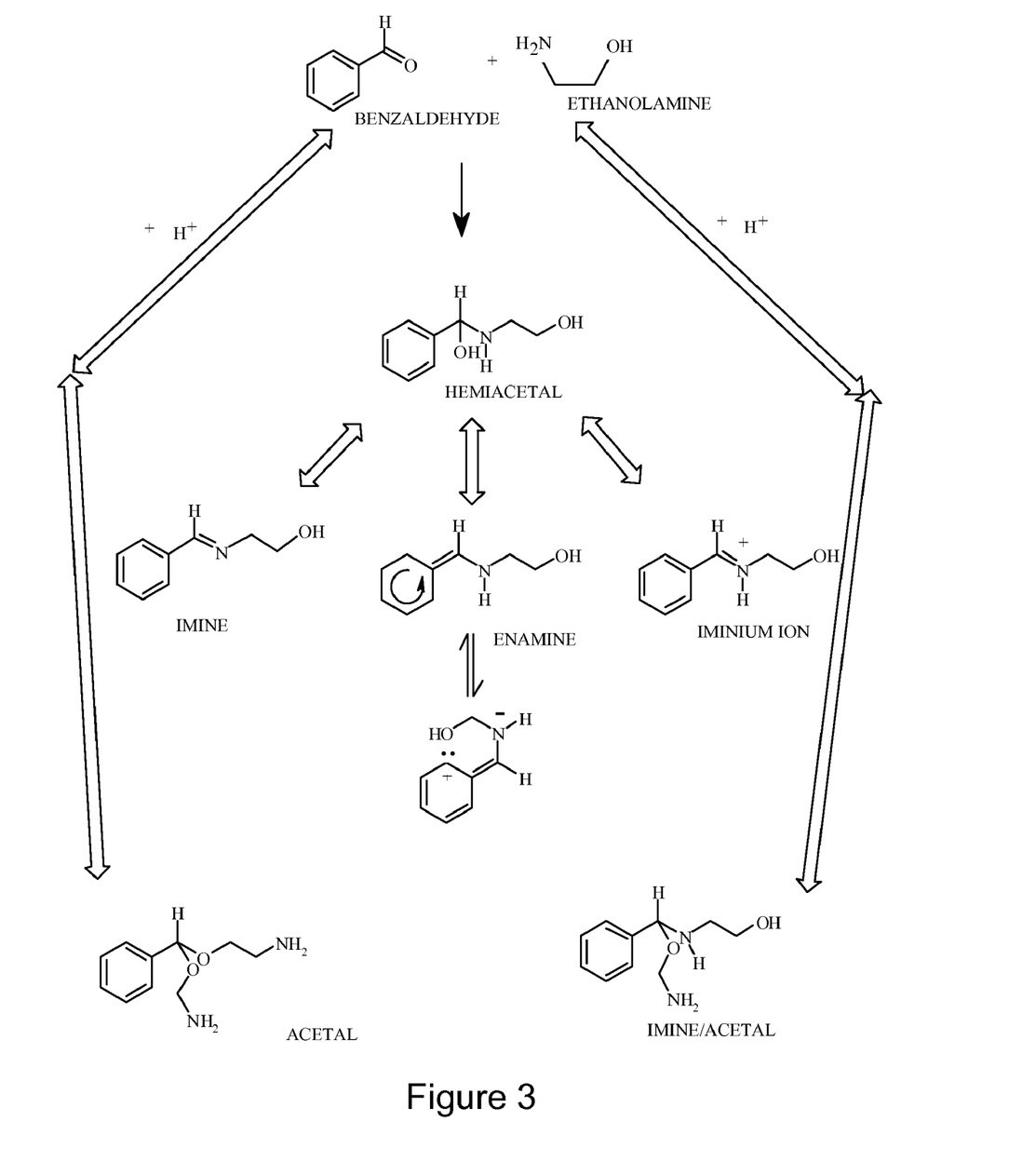
FIG. 3 shows the various products formed upon the reaction of benzaldehyde and ethanolamine.

As noted above, aldehydes can exist in equilibrium with hemiacetals and acetals. Similarly, imine/enamine tautomers are believed to form corresponding acetals, hemi-acetals, and/or amine/acetals. The various products produced by reacting benzaldehyde and ethanolamine are shown in FIG. 3. Observations further suggest that dimers or other polymers (herein, multimers) of aromatic imine compounds are formed.

Just as hemiacetals and acetals are subject to acid/water hydrolysis to reform the aldehyde and alcohol, hydrolysis by anhydrous thiols under acidic conditions establishes an equilibrium between aldols and thioaldols. In this manner, acetals react with hydrogen sulfide to regenerate the aromatic aldehyde starting material and scavenge sulfide.

The present aromatic imine compounds have numerous applications in removing reactive contaminants, e.g., sulfides, from water, oil, fuel, solvents, and other solvents. Some aromatic imine compounds are water soluble, making them ideal for removing hydrogen sulfide and mercaptans from water supplies and contaminated natural waters. Some of the aromatic imine compounds are oil (including fuel and/or non-polar solvents) soluble, partly due to the aromatic ring contributed by the reacting aromatic aldehyde. Benzene, toluene, xylene, and other aromatic compounds are naturally present in oils and fuels and help dissolve other aromatic compounds. Oil solubility also results from resonance structures that minimize the solvent-exposed charge in the imine compounds (particularly resonance structures involving acetals).

A comparison of a particular aromatic imine compounds with conventional sulfide scavenger reagents is described in Example 6 and Table 2. The aromatic imine compounds were about three-times more reactive than conventional nonconjugated imines and triazines. Moreover, less aromatic imine compound than triazine compound (by weight) was required to scavenge the same amount of sulfide. This result is unexpected since triazines have three sulfide-reactive sites, while the present compounds have only one. Organic sulfide molecules formed by aromatic imine compounds are stable and difficult to decompose.

The present aromatic imine compounds are also less bacteriocidal than formaldehyde, glyoxal, and triazines, allowing them to be used in water treatment applications where it is undesirable to kill the bacterial flora in the water. This makes the present compounds ideal for use in open bed processing facilities and bioreactors, which use bacteria to process water-borne contaminants. However, the present compounds can be used in combination with bacteriocidal agents if desired.

These observations demonstrate that the present aromatic imine compounds bind to hydrogen sulfide and mercaptans with high affinity and are less toxic that conventional sulfide scavengers, making them ideal for reacting with and neutralizing malodorous sulfurated compounds without the safety hazards associated with conventional reagents.

III. Synthesis of Aromatic Imine Compounds

Exemplary starting materials and methods of synthesis are described, below.

A. Starting Materials

A large number of aromatic aldehydes are commercially available and suitable for use as described herein. Many are naturally-occurring. Examples include benzaldehyde, p-hydroxybenzaldehyde, mesitylaldehyde, protocatechualdehyde, anisaldehyde, tolualdehyde, cinnamaldehyde, cumaldehyde, salicylaldehyde, thiophenaldehyde, isonicotinaldehyde, furfuraldehyde, vanillin, ethyl vanillin, pyridine aldehyde, pyrimidine aldehyde, phthalaldehyde, nitrobenzaldehyde, resorcylaldehyde, and syringaldehyde. These compounds are widely used to mask noxious odors and for use as perfume bases, albeit conventionally because of their fragrant aromas rather than their ability to scavenge reactive molecules. Testing in support of the present aromatic imine compound demonstrate the aromatic aldehydes possess only weak sulfide scavenging activity and are too fragrant to be used in the field.

The particular aromatic aldehyde selected will likely affect the properties of the resulting aromatic imine compound but not the underlying chemistry and important features of the product. Aromatic aldehydes can be selected to increase the solubility of the product imine compounds in aqueous or organic liquids, e.g., by the selecting charged or non-polar side chains. In some cases it may be desirable to leave a small amount of the aromatic hydrocarbon unreacted, or "add back" a small amount of the same or another aromatic aldehyde, to leave residual aroma in the product.

Primary and secondary amines suitable for use as described herein include but are not limited to ethanolamine, diethanolamine, diglycol-amine, aniline, ethylene diamine, aminoethylethanolamine, ethyl amine, isopropanolamine, dibutyl amine, diethylene triamine, tetraethylene pentamine, methyl anthranilate, and ammonia. Diamines and multiple-amine compounds may also be used. Such compounds have two or more amine groups in their molecule. Common examples are ethylenediamine, triethylenetetramine, tetraethylenepentamine.

Aromatic aldehydes for use in producing the present aromatic imine compounds can be a single species or a mixture of several different species. Similarly, the primary or secondary amines, diamine, or multiple-amine can be a single species or mixture of several species.

In view of the above description, it will be understood that aromatic imine compounds can be referred to as comprising a first portion derived from an aromatic aldehyde lacking an active alpha hydrogen and a second portion derived from an amine or amine derivative.

B. Reactions

A number of syntheses were performed in support of the present compositions and methods. A description of the reactions and their products is described below. Variations and modifications will be apparent. The exemplary syntheses were performed using readily available starting materials in different ratios. Most starting materials are liquids and the reactions are initiated by mixing the indicated amount of each starting material at room temperature or at an elevated temperature. The resulting aromatic imine compounds were tested and proved to be excellent sulfide scavengers.

Reactions between aromatic aldehydes and amines generally appear to be exothermic and reaction temperature affects the properties of the product. For example, a stoichiometrically balanced reaction between benzaldehyde and ethanolamine at a temperature above 140° F. (60° C.) produced a reddish brown reaction product. A reaction maintained below 120° F. (49° C.) produced products that were less colored, i.e., light brown/amber. The color is postulated to be due to oxidation of the aldehyde starting materials or the corresponding portion of an intermediate or product. Slower addition of starting materials reduced the increase in temperature, although an ice bath or more elaborate cooling system should produce similar results faster. Over-addition of an amine in the reaction produced an odorless product. Under-addition of the amine produced a scented product, presumably resulting from unreacted aldehyde.

Exemplary reactions are described, below.

1. Benzaldehyde and Ethanolamine

Figure 4:
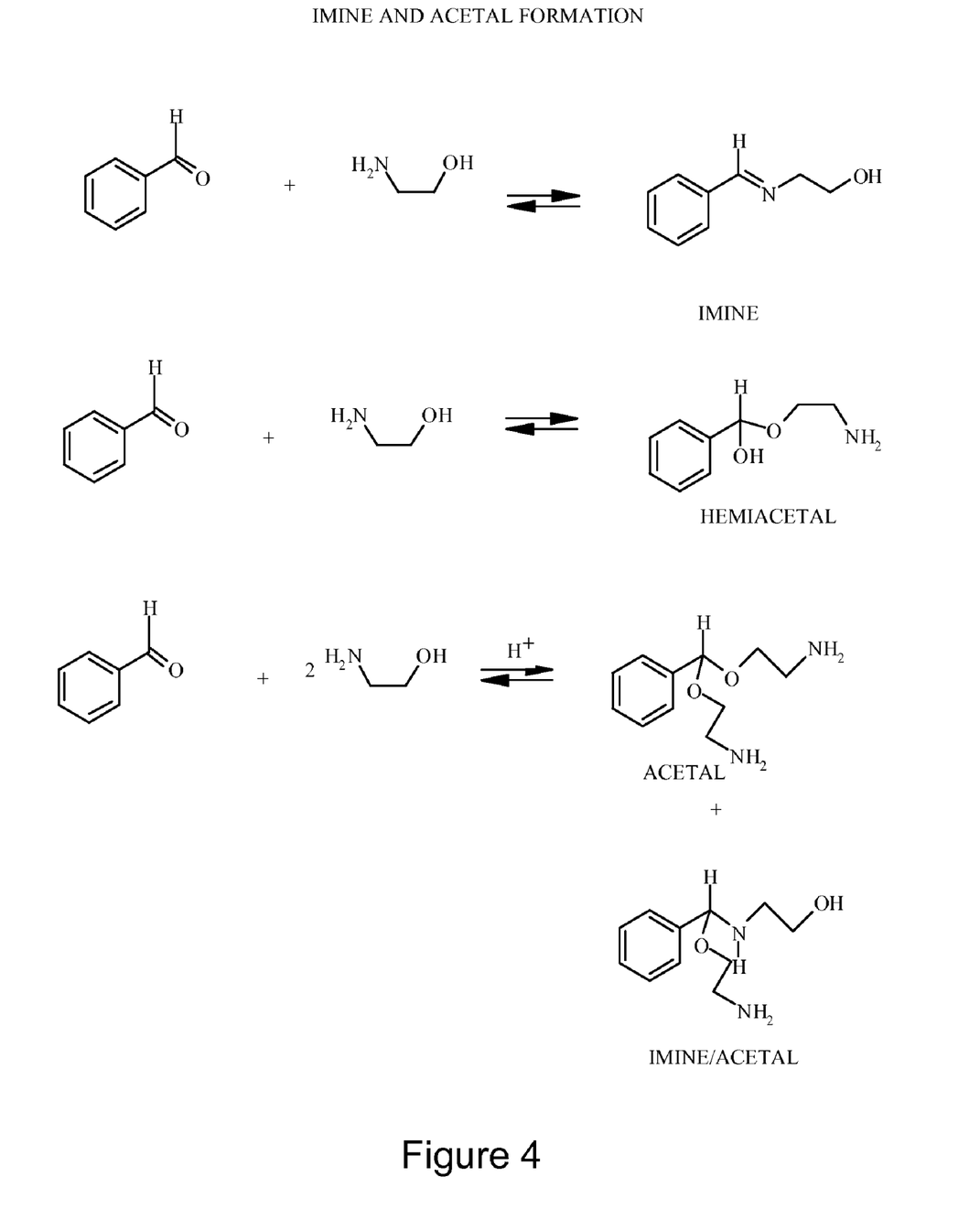
FIG. 4 shows products formed by reacting benzaldehyde and ethanolamine under different conditions.

One readily available aromatic aldehyde starting material is benzaldehyde, which consists of an aromatic ring bound to an aldehyde functional group. The aldehyde alpha carbon is part of the aromatic ring and, therefore, has no active hydrogen available for structural rearrangement. Reactions of benzaldehyde with primary or secondary amines (i.e., with one or two alkyl groups attached to the amine nitrogen) can produce a variety of different compounds, as discussed above. Products formed by reacting benzaldehyde and ethanolamine are shown in FIG. 3. Examples of reactions between benzaldehyde and ethanolamine at different ratios, and in the presence or absence of water, are shown in FIG. 4, and further described in the Examples, which describe reactions at a 2:1 ratio (Example 1), a 1:2 ratio (Example 2), a 1:1 ratio in the presence of water (Example 3), and a 1:1 ratio under anhydrous conditions (Example 4). Formulations 1-3 and 9 in Example 5 provide additional examples of benzaldehyde-ethanolamine reactions.

Figure 5:
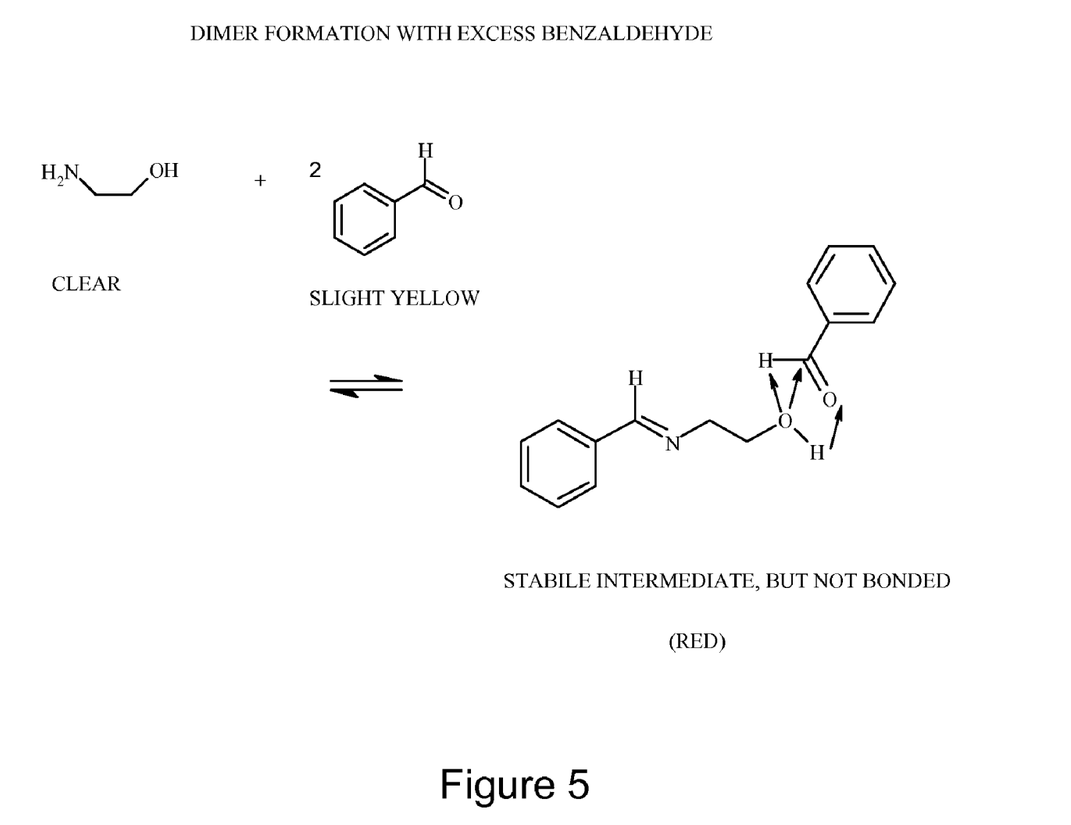
FIG. 5 shows the production of dimers using an excess of aromatic aldehyde.

Under anhydrous conditions, ethanolamine behaves as both an amine and an alcohol. Benzaldehyde reacted with ethanolamine at a 1:1 molar ratio produced about 10-12% oil soluble acetal product (Example 4). The presence of excess ethanolamine (e.g., 2 moles ethanolamine per 1 mole of aromatic aldehyde) appeared to favor the formation of acetals and is believed to lead to the formation of dimers, as shown in FIG. 5. Acetals are insoluble in water but soluble in organic solvents and bases. Production of acetals from benzaldehyde and ethanolamine occurred mainly in the absence of water. Such acetals were stable in basic solution but were susceptible to acidic cleavage to regenerate their aldehyde and alcohol components.

Benzaldehyde reacted with ethanolamine in the presence of water (e.g., about 10%) proceeded most completely to the iminelenamine product, which was water soluble (Example 3; Formulation 11 in Example 5; and FIGS. 2 and 3).

2. Benzaldehyde and Diamines/Multiple-Amine Compounds

Figure 6:
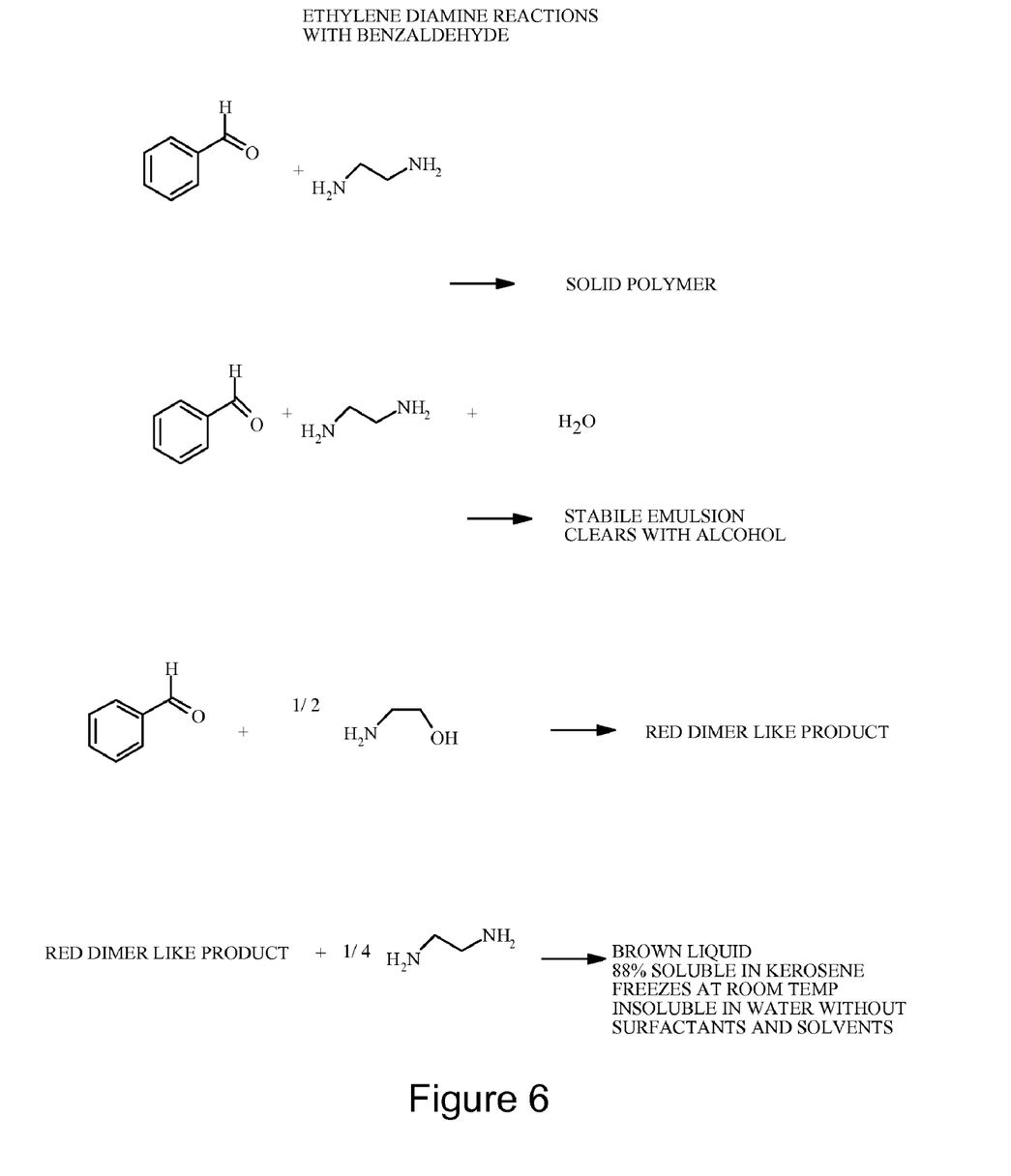
FIG. 6 shows the products formed upon the reaction of benzaldehyde and ethylene diamine.

Diamines and multiple-amine compounds have two or more amine groups. Common examples are ethylenediamine, triethylenetetramine, and tetraethylenepentamine. When such compounds are reacted with aromatic aldehydes, the molar ratio should be one diamine molecule to two aldehyde molecules to obtain stoichiometric concentration of reactants. Formulations 4 and 8 of Example 5 exemplify such compounds. FIG. 6 shows the products obtained under different reaction conditions.

Under anhydrous conditions, low temperature reactions produce monomers, while higher temperature reactions produce a low melting point solid (likely polymerized). This latter type of product may be useful as a deodorizer in an open air situations or in turbulent flow tanks because they are not significantly soluble in water. Such polymers may be dissolved in solvents and used as a starting material for further synthesis.

When aromatic aldehydes are reacted with diamines in the presence of water, they produce different products than when reacted anhydrously. Aromatic imine products produced in the presence of water are soluble in alcohol and form water emulsions, making them suitable for use as scavengers in various contaminated liquids, including water, oils, fuels, and solvents (e.g., Formulation 5 in Example 5).

If an aromatic aldehyde is reacted with ethanolamine at only half the molar concentration necessary to create the aromatic imine compounds, and then finished with the diamine, another class of aromatic imine compounds is formed have a low melting point, being soluble in organic solvents, and being only slightly soluble in water (not shown).

In a particular example, benzaldehyde reacted with monoethanolamine at a molar ratio of two aldehydes to one monoethanolamine, and then reacted with ethylenediamine at a molar ratio of 1 mole benzaldehyde to 0.25 moles ethylenediamine after the reaction has cooled, produces a product having a melting point below 0° F. and being 80% soluble in diesel fuel (Example 5, Formulation 5). The product was very reactive to hydrogen sulfide (Table 1).

Reactions involving benzaldehyde and ethylene diamine are summarized in FIG. 6. An aromatic aldehyde can be reacted with a plurality of diamines and/or multiple-amine compounds, which are combined in a single reaction, added separately, or added sequentially, to the aromatic aldehyde. Combinations and variations in starting materials can be used to produce many different aromatic imine compounds.

3. Reactions Using Other Naturally-Occurring Aromatic Aldehydes

Figure 7:
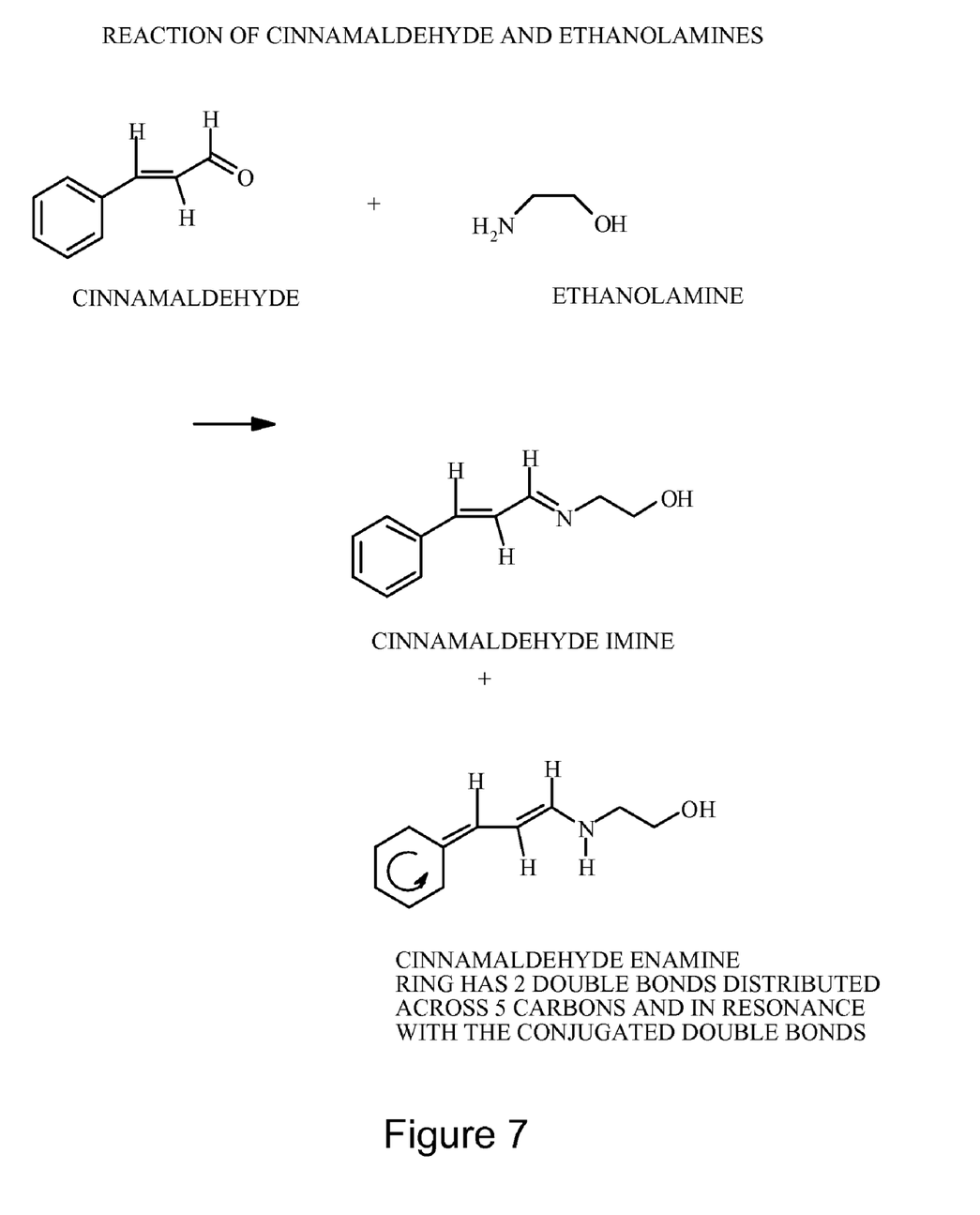
FIG. 7 shows products formed upon the reaction of cinnamaldehyde and ethanolamine.

Another exemplary aromatic aldehyde starting material is cinnamaldehyde. Although the aldehyde group in the cinnamaldehyde molecule is not attached directly to the aromatic ring, it includes an allylic carbon which is more reactive than a benzyl carbon. Cinnamaldehyde can be reacted with, e.g., ethanolamine to produce an enamine compound with reactivity similar to that of the present aromatic imine compounds. A reaction involving cinnamaldehyde is shown in FIG. 7.

Figure 8:
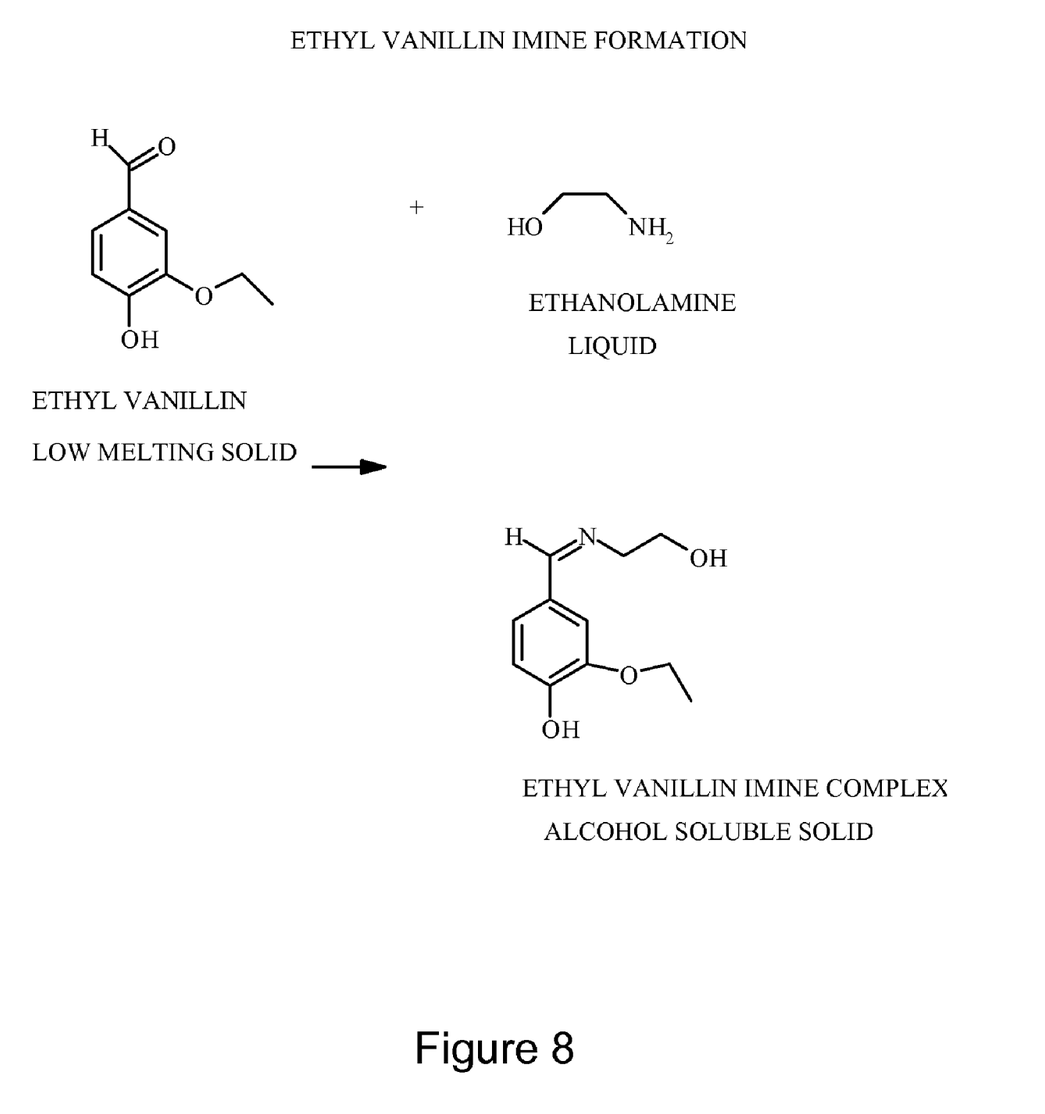
FIG. 8 shows the products formed upon the reaction of vanillin and ethanolamine.

Further aromatic aldehyde starting materials include vanillin and ethyl vanillin. These aromatic aldehydes are similar to benzaldehyde but include an additional hydroxyl group at the para position on the benzene ring and an ether at the meta position. FIG. 8 shows a reaction involving ethyl vanillin and the reaction products produced. Other naturally occurring aromatic aldehydes can be used in the same manner. Availability and scent are considerations in selecting an aromatic aldehyde, or mixture of aromatic aldehydes, as a starting material.

4. Aromatic Aldehyde Reactions with Other Amines

Figure 9:
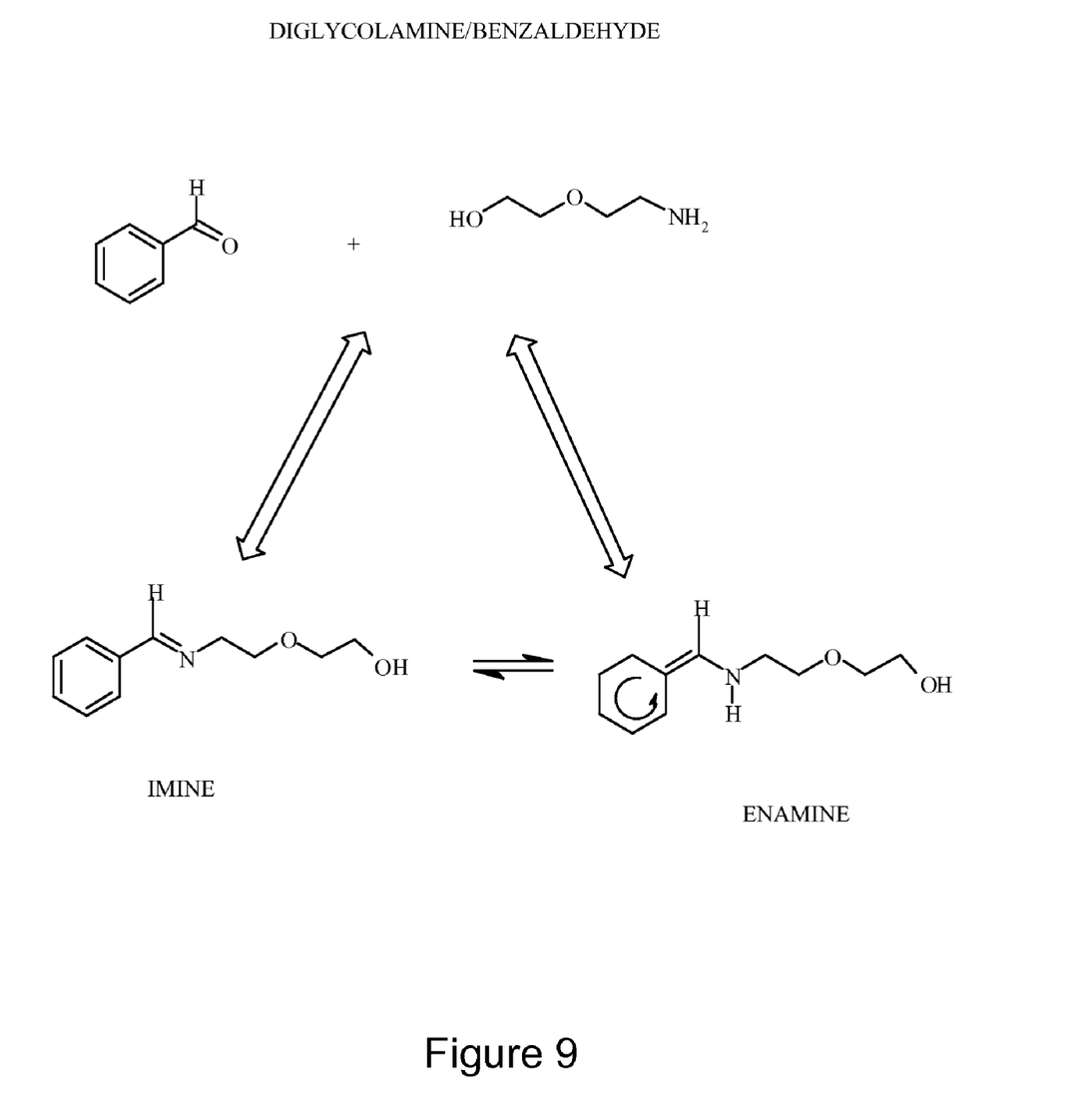
FIG. 9 shows the products formed upon the reaction of benzaldehyde and diglycol-amine.
Figure 10:
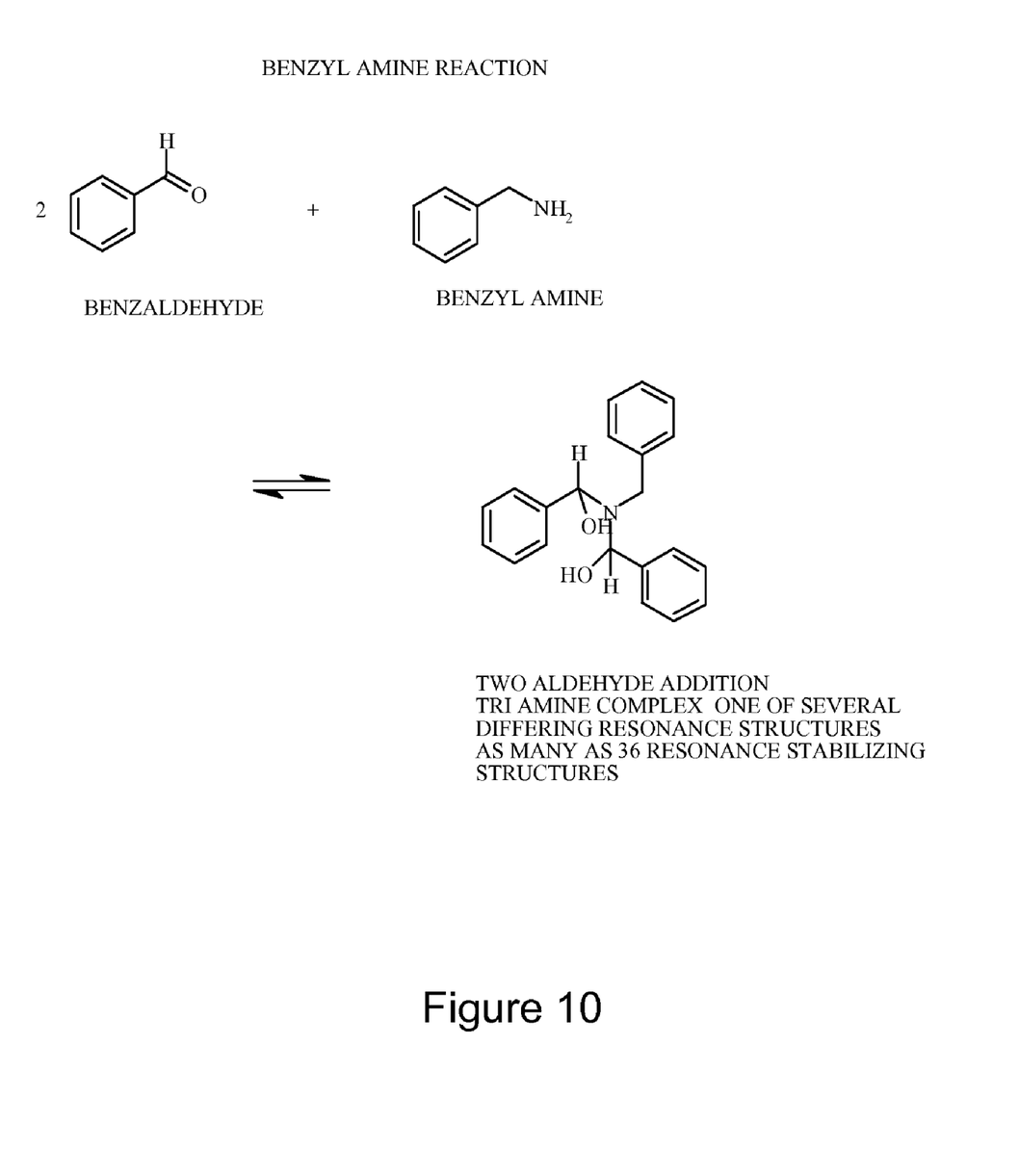
FIG. 10 shows the products formed upon the reaction of benzaldehyde and benzyl amine.

Aromatic aldehydes can be reacted with amines such as diglycol-amine (as shown in FIG. 9) and benzylamine (as shown in FIG. 10). The reaction with diglycol-amine produces an imine/enamine, as in the case of the reaction with monoethanolamine. The reaction with benzylamine produces a diazine compound with a variety or resonance structures.

5. Benzaldehyde and Methanol

A related reaction is that of an aromatic aldehyde with an alcohol to produce an aromatic acetal. Acetals form when the reaction is performed in the presence of very little water. Generally, one mole of aromatic aldehyde reacts with two moles of alcohol in the presence of acid to form a corresponding acetal.

In one example, benzaldehyde was reacted with methanol in a molar ratio of one mole benzaldehyde to two moles methanol to two moles phosphoric acid. This reaction corresponds to Formulation 7 in Example 5. The product was neutralized with monoethanolamine to a final basic pH of 10. The resulting product had an ether-like aroma distinct from that of benzaldehyde or methanol. The neutralized phosphates were separated from the acetal product using a separatory funnel. Residual methanol was boiled off, leaving a syrupy red/orange liquid that was insoluble in water but soluble in alcohol. This aromatic acetal was effective as a hydrogen sulfide scavenger (Table 1).

IV. Triazine Synthesis

As described above and in Example 6, the present aromatic imine compounds are more effective than triazines for scavenging reactive compounds and less toxic to bacteria. Nonetheless, the present aromatic imine compounds can be used for the synthesis of triazine compounds by reacting them with glyoxal, or other dialdehydes and primary amines.

Conventional methods for producing triazines use formaldehyde or glyoxal and an ethanolamine to produce molecules with three carbon-nitrogen double-bonds. When aromatic imine compounds are used as the base for producing triazines, the chemistry is different, reflecting the tautomeric and resonance-stabilized intermediates of the aromatic imine compounds. Conventional reactions that create triazines do not include a reaction with the alcohol side of ethanolamine to produce acetals and crossed amine/acetals, due to lack of resonance stability in the more polar formaldehyde molecule.

Two reactions were performed in support of these methods. In a first reaction triazines were produced by reacting equal molar quantities of the present aromatic imine compounds and glyoxal and twice the molar amount of monoethanolamine (i.e., 1:1:2; Formulation 12 in Example 4). The reaction was exothermic and yielded a red/brown liquid triazine, which was a hydrogen sulfide scavenger (Table 1). In a second reaction, Sulfree OS (i.e., Formulation 2 in Example 5) was reacted with monoethanolamine, glyoxal, SXS-40, and water to produce an 80% triazine solution. Triazines are known sulfide scavengers and are known to have bacteriocidal activity. The triazines produced from the described aromatic imine compounds are expected to posses these properties.

Such reactions allow the production of triamines without the need to handle formaldehyde, which is toxic to humans and non-human animals. The present methods include the production of triazines from aromatic imine compounds and the present compositions include triazines produced from aromatic imine compounds.

V. Use of Surfactants

While many of the present compounds are soluble in water and most all are soluble in organic solvents, it may still be desirable to use the compounds in combination with surfactants. Surfactants can enhance the solubility of the present compounds in fuel or water. For example, when sweetening gas, fuels, solvents, or water, surfactant addition enhances performance by promoting interactions between the aromatic imine compound and hydrogen sulfide. An amount of surfactant in the range of from about 0.5% to about 5% is considered optimum. Even a lower range of concentrations may be suitable for fluorinated surfactants, which can be used to wet the subject liquid and allow greater contact without foaming. An excessive amount of surfactant, or the selection of an inappropriate surfactant, can lead to undesirable foaming.

In-line injection systems using the present compositions for scrubbing gas streams benefit from the addition of surfactants. Surfactants can also be added to reactions producing aromatic imine compounds, since they are not expected to interfere.

VI. Liquid and Gas Phase Applications

The present aromatic imine compounds can be used in both gas and liquid application, using such equipment as spray columns, bubble columns, in line injectors, in-line mixers, or site specific injectors and gas/liquid contacting devices. These can be in-line, in parallel, in sequence, or in any functional arrangement. Multiple injection sites can be used depending on volume of gas to be treated.

In this manner, the present compounds can be used to remove sulfide from fuels, solvents, sour gas, sulfide contaminated liquid water and water vapor, contaminated natural gas, etc. The compounds may be used as a primary means of removing sulfides or to "polish" gases or liquids downstream of, e.g., an alkanolamine sulfur recovery plant that fails to adequately reduce hydrogen sulfide levels to those required by law or desired for health and aesthetics.

In one example, the present compounds are used to treat sour crude oil and/or hydrocarbon streams in oil refineries. In another example, the present compounds are used to treat sewer gas in drains and treatment facilities. In other embodiments, the compounds are used to sweeten and control odor in restaurants grease traps, garbage collection facilities, animal care and housing facilities, morgues, restrooms, portable toilets, military barracks, etc. The compounds may be in the form of an air freshener device, wherein an aromatic imine compound is immobilized on a solid support and/or a solid or semi-solid aromatic imine compounds, as are described herein.

In another embodiment, the present compounds are provided in oil or a suitable solvent for use as a surface sulfide scavenger reagent. Such gas or liquid aromatic aldehyde reagents are useful for removing sulfide from the surface of contaminated equipment and structures, including but not limited to oil and natural gas equipment.

In other embodiments, the present compounds can be dispersed in gas can be sprayed directly into air or other sulfide contaminated gases (including air, nitrogen, nitrous oxide, natural gas, etc.). The present compounds can also dispersed in liquid oil or a suitable aqueous or organic solvent and applied to a filter or other matrix to be used as an airborne sulfide scavenger. The matrix-bound aromatic aldehyde can be provided in the form of particles for filtering moving air (e.g., in the form of a filtering matrix). The particles can be beads, a filter matrix (e.g., glass fibers, cloth, high-particulate air (HEPA), etc.). Devices comprise such particles are useful for removing sulfides present in air or other gases (including natural gas) in the form of e.g., an in-line sulfide-scavenging filter/matrix. Oils or other suitable solvents can also be applied to a pad or other porous material, for use in a static air sulfide scavenging devices. An exemplary device is in the form of an air freshener.

The present aromatic imine compounds can be used in conjunction with cleaning agents, surfactants and other building products. The present compounds can generally react with sulfide without reacting with the cleaning agents.

The following examples relate to the synthesis and characterization of particular aromatic imine compounds. These examples are intended to be illustrative. Further aspects of the present compositions and methods will be apparent to one skilled in the art in view of the present description.

EXAMPLES

Example 1

Benzaldehyde and Monoethanolamine (2:1)

Benzaldehyde and monoethanolamine were reacted at a molar ratio of 2:1, (i.e., 1 mole benzaldehyde to 0.5 mole monoethanolamine) to produce aromatic imine compounds. The reaction and reaction products are shown in FIGS. 3 and 4. A red-colored chemical intermediate (i.e., formed as the monoethanolamine was being added) was produced from colorless starting materials. Without being limited to a theory, it is postulated that a meta-stable dimer consisting of two molecules of benzaldehyde and one molecule of monoethanolamine was produced (FIG. 6). The possibility of further polymerization cannot be excluded. The red color is noteworthy. As this stage in synthesis (a 2:1 ratio), the solution continued to smell heavily of benzaldehyde. Adding the second of two equal portions of monoethanolamine (to achieve a 1:1 ratio) eliminated the benzaldehyde aroma and changed the color of the solution to light amber (much as before).

Example 2

Benzaldehyde and Monoethanolamine (1:2)

Benzaldehyde and monoethanolamine were reacted at a molar ratio of 1:2 to produce aromatic imine compounds. The reaction and reaction products are shown in FIGS. 3 and 4. The resulting solution was darker in color than that of Example 1 colored and had no benzaldehyde aroma.

Example 3

Benzaldehyde and Monoethanolamine (1:1) in 10% Water

Benzaldehyde and monoethanolamine were reacted at a molar ratio of 1:1 in the presence of 10% water to produce aromatic imine compounds. The reaction and reaction products are shown in FIGS. 3 and 4. The resulting product is highly water soluble without the addition of surfactants.

Example 4

Benzaldehyde and Monoethanolamine (1:1), Anhydrous

Benzaldehyde and monoethanolamine were reacted at a molar ratio of 1:1 under anhydrous conditions to produce aromatic imine compounds. The reaction and reaction products are shown in FIGS. 3 and 4. The resultant mixture is about 90% water soluble, without the addition of surfactants. The resultant mixture was also about 12% soluble in diesel fuel.

Example 5

Formulations for Testing Against Hydrogen Sulfide

The following 13 formulations were made and tested for their ability to remove $H_2S$ from water.

Formulation 1 (Sulfree OS, Odorized Version):

| | |
|---|---|
| Benzaldehyde | 60% |
| Monoethanolamine | 40% |

Observations: Produced a light brown liquid with a small amount of benzaldehyde aroma.
Results: Effective (Table 1).
Formulation 2 (Sulfree OS):

| | |
|---|---|
| Benzaldehyde | 58% |
| Monethanolamine | 42% |

Observations: Produced a light brown liquid with slight amine odor. Flashpoint of product (80° F.; 26.7° C.) lower than flashpoint of benzaldehyde (140° F.; 60° C.) and monoethanolamine (200° F.; 93° C.).
Results: Effective (Tables 1, 2, and 3).
Solubility: 12% in kerosene.
Formulation 3:

| | |
|---|---|
| Benzaldehyde | 75% |
| Monoethanolamine | 25% |

Observations: Produced a fragrant red liquid—high benzaldehyde odor.
Results: Effective (Table 1).
Formulation 4:

| | |
|---|---|
| Benzaldehyde | 67% |
| Monoethanolamine | 20% |
| Ethylene diamine | 13% |

Observations: Produced a brown liquid with an amine odor.
Results: Effective (Table 1).
Solubility: 80% in kerosene.

Formulation 5:

| | |
|---|---|
| Ethylene diamine | 34% |
| Water | 11% |
| Benzaldehyde | 55% |

Observations: Produced a light yellow liquid with an amine odor.
Results: Effective (Table 1).
Solubility: Produced emulsions in water.
Formulation 6:

| | |
|---|---|
| Benzaldehyde | 46% |
| Diglycol-amine | 54% |

Observations: Produced an amber liquid with an amine odor.
Results: Effective (Table 1).
Solubility: Dissolved 100% in water.
Formulation 7: (see Acetal Formation, Below)

| | |
|---|---|
| Benzaldehyde | 41% |
| Methanol | 27% |
| Phosphoric acid 85% | 18% |
| Monoethanolamine | 14% |

Notes/observations: Neutralized with monoethanolamine to a final pH of 10. Ether-like aroma and two phases. Neutralized phosphates separated from acetal using separatory funnel. Residual methanol boiled off, leaving syrupy red/orange liquid insoluble in water but soluble in alcohol. Yielded about 60% of the acetal, reddish/pink liquid with an ether odor.
Results: Effective (Table 1).
Solubility: Insoluble in water but soluble in alcohol.
Formulation 8:

| | |
|---|---|
| Benzaldehyde | 44% |
| Monoethanolamine | 16% |
| Tetraethylenepentamine | 40% |

Observations: Produced a red liquid that was sparingly soluble in water and reeked of benzaldehyde.
Results: Effective (Table 1).
Formulation 9:

| | |
|---|---|
| Benzaldehyde | 41% |
| Monoethanolamine | 59% |

Observations: Produced a brown liquid with an amine odor.
Results: Effective (Table 1).
Formulation 10:

| | |
|---|---|
| Ethyl vanillin | 71.2% |
| Monoethanolamine | 28.8% |

Observations: Produced a solid/liquid combination—melting under 80° C.
Results: Effective (Table 1).
Formulation 11:

| | | |
|---|---|---|
| Benzaldehyde | 28.8% |
| Monoethanolamine | 23.5% |
| Water | 47.7% |

Observations: Produced a water soluble light brown/amber liquid.
Results: Effective (Table 1).
Formulation 12: (Triazine Formation)

| | | | | | |
|---|---|---|---|---|---|
| Benzaldehyde | 21.5% | or | Benzaldehyde | 37% |
| Monoethanolamine | 44.5% | | Monoethanolamine | 33% |
| Glyoxal 40% | 34% | | Glyoxal 40% | 30% |

Observations: Both compositions were used. Produced a red/brown liquid with mild amine odor.
Results: Effective (Table 1; 37% Benzaldehyde formulation)
Formulation 13:

| | |
|---|---|
| Benzaldehyde | 63% |
| Benzyl Amine | 37% |

Observations: Produced a light brown solution with an amine odor.
Results: Effective (Table 1).
Solubility: Produces emulsions in surfactant/water solutions.
Formulation 14 (Sulfree WS):

| | |
|---|---|
| Benzaldehyde | 36% |
| Monoethanolamine | 24% |
| Water | 40% |

Observations: Produced a light brown solution with an amine odor.
Results: Effective (Tables 2 and 3).
Solubility: Water soluble.

Formulation 15 (Triazine Formation):

| | |
|---|---|
| Sulfree OS | 32.76% |
| Monoethanolamine | 20.89% |
| Glyoxal (40%) | 27% |
| SXS-40 | 2% |
| Water | 17.35% |

Observations: Produced an 80% triazine solution.
SXS-40=sodium xylene sulfonate.
The results obtained using the above formulations to remove a known amount of $H_2S$ from water are shown in Table 1.

TABLE 1

$H_2S$ removal data using several formulations.

| Formulation | $H_2S$ start | $H_2S$ final |
|---|---|---|
| 1 | 1000 ppm | 400 ppm |
| 2 | 1000 ppm | 400 ppm |
| 3 | 1000 ppm | 434 ppm |
| 4 | 1000 ppm | 400 ppm |
| 5 | 1000 ppm | 550 ppm |
| 6 | 1000 ppm | 500 ppm |
| 7 | 900 ppm | 451 ppm |
| 8 | 900 ppm | 550 ppm |
| 9 | 900 ppm | 559 ppm |
| 10 | 900 ppm | 235 ppm |
| 11 | 900 ppm | 550 ppm |
| 12 | 900 ppm | 250 ppm |
| 13 | 900 ppm | 356 ppm |

Example 6

Comparison with Conventional Methods

The results obtained using two of the present imine compounds (Sulfree OS and Sulfree WS; Example 5, Formulations 2 and 14, respectively), triazine, SULFIX (a triazine scavenger; Sulfa-Check, TX, USA), or glyoxal to remove 1,000 ppm $H_2S$ from water are shown in Table 2. The aromatic imine compounds were also tested against another triazine scavenger, Busan 5103 (Buckman Laboratories, Inc., Memphis, Tenn., USA), with similar results (not shown). An overall comparison of the features of the present aromatic imine compounds and conventional compositions is shown in Table 3.

TABLE 2

Results of several treatments against $H_2S$ dissolved in water

| | Residual $H_2S$ | | | | | Lead acetate paper test | |
|---|---|---|---|---|---|---|---|
| Product | I 2 Titration | Chemetrics (colormetric) | Outside Lab | Chemetrics (colormetric) | Smell | Head space | Liquid |
| Sulfree WS | 212 ppm | 250 ppm | 664 ppm | 0 ppm | fruity odor | white | white |
| Sulfree OS | 544 ppm | 400 ppm | 651 ppm | 0 ppm | fruity odor | white | white, (yellow) |
| Triazine | 660 ppm | 600 ppm | 728 ppm | 300 ppm | sulfur/mercaptan | yellow/brown | brown |
| Sulfix | 671 ppm | 500 ppm | not tested | not tested | sulfur/mercaptan | not tested | brown |
| Glyoxal | 350 ppm (yellow) | 0 ppm | 240 ppm | 0 ppm | strong sulfur/mercaptan | brown/black | yellow/orange |

TABLE 3

Comparison of features between the present compositions and existing compositions.

| FEATURE | Sulfree WS | Sulfree OS | Busan 5103 | Sulfix | Glyoxal |
|---|---|---|---|---|---|
| Safe to use | safe | safe | some hazards | some hazards | some hazards |
| Formaldehyde | no | no | 100 ppm | 100 ppm | 100 ppm |
| Different formulations | yes | yes | yes | yes | no |
| Oil Solubility | >10% | >80% | no | no | no |
| Polymerization | no | no | yes | yes | yes |
| Recommended dosage | 2-5:1 | 2-5:1 | 2-5:1 | 2-5:1 | 10:01 |
| Stable | yes | yes | yes | yes | no |
| Production of insoluble solids in-line | no | no | yes | yes | yes |
| Reactivity* | 1 | 1.1 | 1.3 | 1.2 | 1 |
| Reactive at ambient temperature | yes | yes | yes | yes | yes |
| Strong bonding to $H_2S$ | yes | yes | yes | yes | no |
| Eliminates treatment step | yes | yes | no | no | no |
| Odor/aroma | yes | yes | no | no | no |
| Deodorizes | yes | yes | no | no | no |
| Sensitizing chemical | no | no | yes | yes | yes |
| Toxicity | no | no | no | yes | no |
| Mutagenicity | no | no | yes | yes | yes |
| Carcinogenicity | no | no | yes | yes | yes |
| RCRA Hazardous Waste | no | no | no | no | yes |

*1 is highest

What is claimed is:

1. A method for removing sulfide from a sulfide-containing fluid comprising the step of contacting the fluid with an aromatic imine composition produced by reacting benzaldehyde and monoethanolamine with at least 10% added water by weight of the reaction solution, resulting in a composition having a substantially reduced amount of acetal relative to an aromatic imine composition formed by reacting benzaldehyde and monoethanolamine under similar conditions, but in the absence of added water, thereby removing sulfide from the fluid via reaction with the aromatic imine composition.

2. The method of claim 1, wherein the fluid is waste water in a water-treatment plant.

3. The method of claim 1, wherein the fluid is waste water in a sewage plant.

4. The method of claim 1, wherein the fluid is natural gas.

5. The method of claim 1, wherein the fluid is a liquid petroleum product.

* * * * *